(12) United States Patent
Kapil et al.

(10) Patent No.: US 11,030,744 B2
(45) Date of Patent: Jun. 8, 2021

(54) DEEP LEARNING METHOD FOR TUMOR CELL SCORING ON CANCER BIOPSIES

(71) Applicant: Definiens AG, Munich (DE)

(72) Inventors: Ansh Kapil, Munich (DE); Nicolas Brieu, Munich (DE)

(73) Assignee: AstraZeneca Computational Pathology GmbH, Munich (DE)

(*) Notice: Subject to any disclaimer, the term of this patent is extended or adjusted under 35 U.S.C. 154(b) by 87 days.

(21) Appl. No.: 16/452,511

(22) Filed: Jun. 25, 2019

(65) Prior Publication Data

US 2019/0392580 A1 Dec. 26, 2019

Related U.S. Application Data

(60) Provisional application No. 62/690,329, filed on Jun. 26, 2018.

(51) Int. Cl.
*G06T 7/00* (2017.01)
*A61B 5/00* (2006.01)
*G06K 9/00* (2006.01)

(52) U.S. Cl.
CPC .......... *G06T 7/0012* (2013.01); *A61B 5/7267* (2013.01); *G06K 9/0014* (2013.01); *G06K 9/00147* (2013.01); *G06T 2200/24* (2013.01); *G06T 2207/20081* (2013.01);
(Continued)

(58) Field of Classification Search
CPC .............. G06T 7/0012; G06T 2200/24; G06T 2207/20081; G06T 2207/20084; G06T 2207/30024; G06T 2207/30061; A61B 5/7267; G06K 9/0014; G06K 9/00147; G06K 2209/05; G06K 9/6267
See application file for complete search history.

(56) References Cited

U.S. PATENT DOCUMENTS

| 2017/0076448 A1* | 3/2017 | Chen | G06K 9/00147 |
| 2019/0256546 A1* | 8/2019 | O'Neill | A61K 9/0053 |
| 2019/0347465 A1* | 11/2019 | Dupouy | G06K 9/00127 |

OTHER PUBLICATIONS

Hernandez et al., "Using Deep Learning for Segmentation and Counting within Microscopy Data," Feb. 28, 2018, Stanford, arXiv:1802.10548v1 (6 pages).

(Continued)

*Primary Examiner* — Chuong A Ngo
(74) *Attorney, Agent, or Firm* — Imperium Patent Works; Darien K. Wallace

(57) ABSTRACT

A score of a histopathological diagnosis of cancer is generated by loading an image patch of an image into a processing unit, determining how many pixels of the image patch belong to a first tissue, processing additional image patches cropped from the image to determine how many pixels of each image patch belong to the first tissue, computing the score and displaying it along with the image on a graphical user interface. The image patch is cropped from the image of a slice of tissue that has been immunohistochemically stained using a diagnostic antibody. The first tissue comprises tumor epithelial cells that are positively stained by the diagnostic antibody. Determining how many pixels belong to the first tissue is performed by processing the image patch using a convolutional neural network. The score of the histopathological diagnosis is computed based on the total number of pixels belonging to the first tissue.

25 Claims, 7 Drawing Sheets

(52) U.S. Cl.
CPC .............. *G06T 2207/20084* (2013.01); *G06T 2207/30024* (2013.01); *G06T 2207/30061* (2013.01)

(56) References Cited

OTHER PUBLICATIONS

Long et al., "Fully Convolutional Networks for Semantic Segmentation," UC Berkeley, 2015 (10 pages).
Noh et al., "Learning Deconvolution Network for Semantic Segmentation," ICCV, Dept. Computer Science & Engineering, Postech, Korea, pp. 1520-1528 (9 pages).
Havaei et al., "Brain tumor segmentation with Deep Neural Networks," Medical Image Analysis, vol. 35, Jan. 1, 2017 XP029801693, pp. 18-31 (14 pages).
Hernandez et al., "Using Deep Learning for Segmentation and Counting within Microscopy Data," Feb. 28, 2018, Stanford, arXiv:1802.10548v1, XP081213794 (6 pages).
Le et al., "Patch-Based Convolutional Neural Network for Whole Slide Tissue Image Classification," Mar. 6, 2016, arXiv:1504.07947v5, XP055523985 (10 pages).
Li et al., "Brain Tumor Segmentation Using an Adversarial Network," Feb. 17, 2018, Springer Int'l Publ. LNCS 10670, pp. 123-132 XP047464663 (10 pages).
Riku et el., "Antibody-supervised deep learning for quantification of tumor-infiltrating immune cells in hematoxylin and eosin stained breast cancer samples," Journal of Pathology Informatics, vol. 7, No. 38, Sep. 1, 2016 XP055587403 (14 pages).
Extended European Search Report dated Nov. 15, 2019 by the European Patent Office in the European patent application EP19182560.3 that claims priority to this application (10 pages).

\* cited by examiner

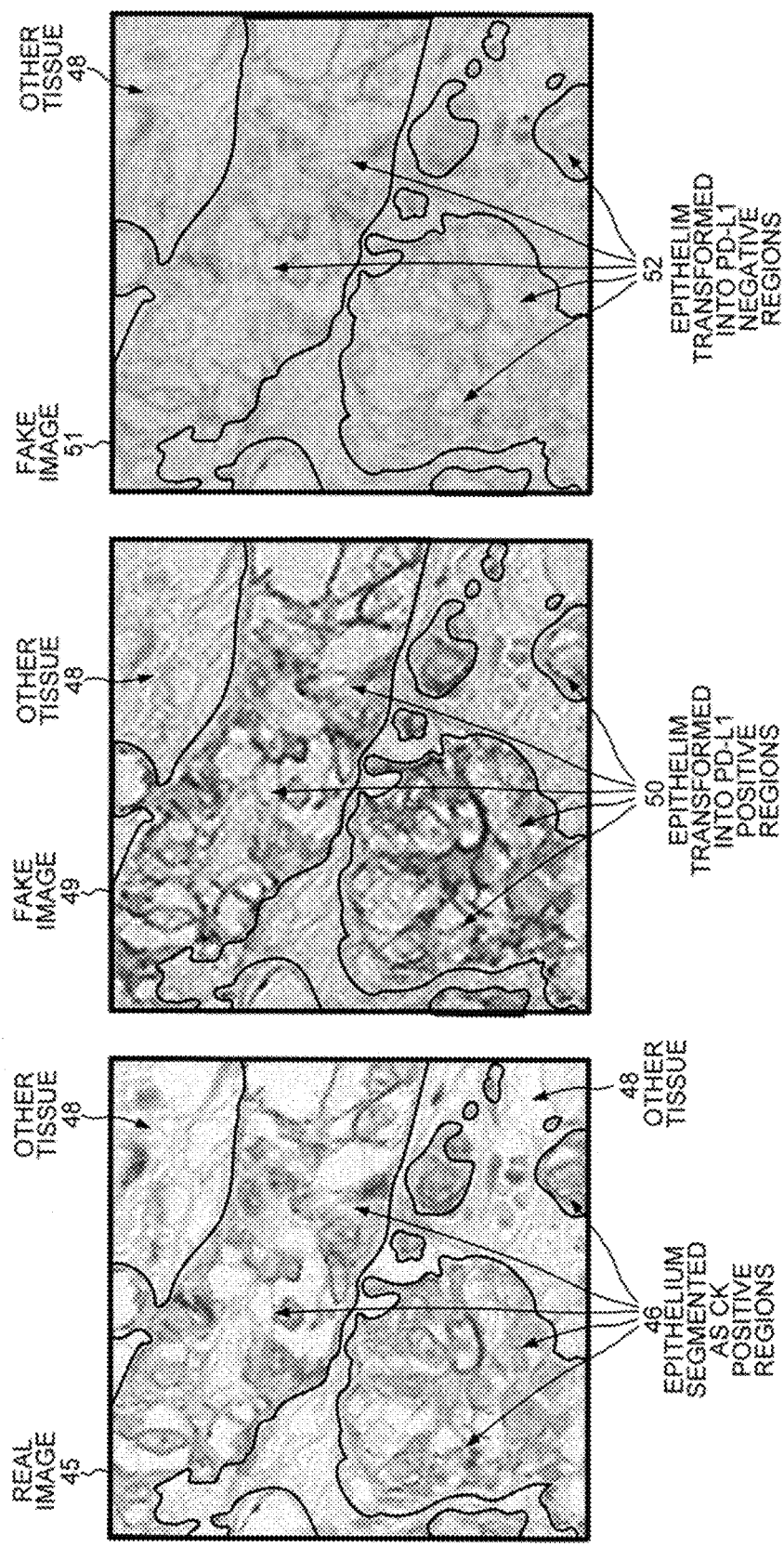

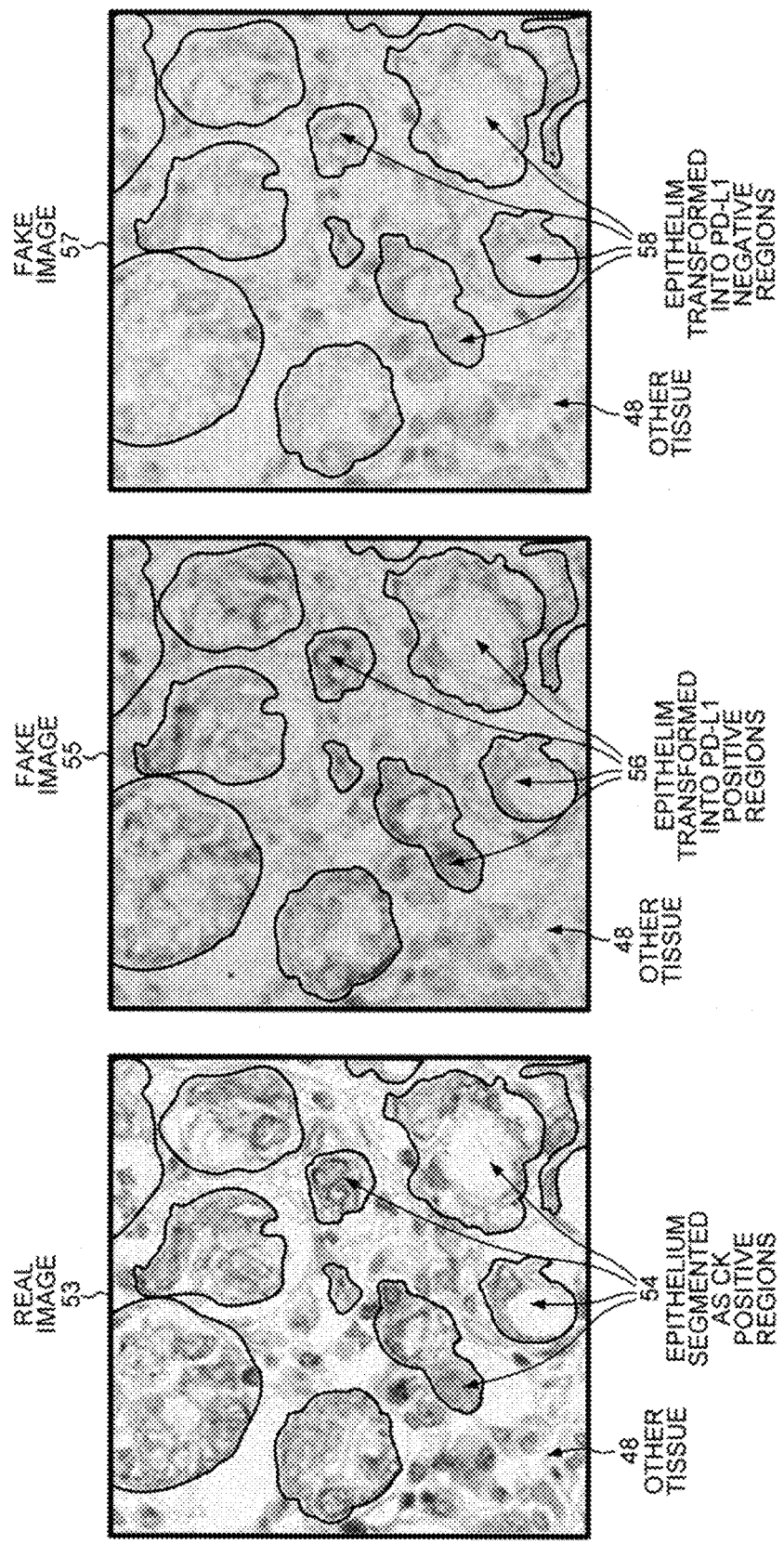

DEEP LEARNING METHOD FOR TUMOR CELL SCORING ON CANCER BIOPSIES

CROSS REFERENCE TO RELATED APPLICATIONS

This application claims the benefit under 35 U.S.C. § 119 of provisional application Ser. No. 62/690,329, entitled "A Semi-Supervised Deep Learning Method for PD-L1 Tumor Cell Scoring on Non-Small-Cell-Lung-Cancer Biopsies", filed on Jun. 26, 2018. The subject matter of provisional application Ser. No. 62/690,329 is incorporated herein by reference.

TECHNICAL FIELD

The present invention relates to a method for generating a score of a histological diagnosis of a cancer patient by training a model to determine how many pixels of a digital image belong to a tissue that has been positively stained by a diagnostic antibody.

BACKGROUND

Identifying tumor regions in digital images of cancer tissue is often a prerequisite to performing diagnostic and treatment measures, such as classifying cancers using standard grading schemes. The digital images of tissue slices used in histopathology are very large. Individual images require gigabytes to store. Manual annotation of the tumor regions in whole slides through the visual assessment of a pathologist is laborious considering the high volume of data. Therefore, "chemical annotation" has been used to substitute the marking of tumor regions by a pathologist with image recognition of regions stained by biomarkers that identify tissue that tends to be cancerous. Annotating tumor regions using specific antibody staining decreases the subjectivity of the pathologist's evaluation and accelerates the otherwise tedious process. Immunohistochemical (IHC) staining can be used to distinguish marker-positive cells that express a particular protein from marker-negative cells that do not express the protein. IHC staining typically involves multiple dyes, which includes one or more dyes connected to protein-specific antibodies and another dye that is a counterstain. A common counterstain is hematoxylin, which labels DNA and thus stains nuclei.

A protein specific stain or biomarker can be used to identify the regions of the tissue that are likely cancerous. For example, a biomarker that stains epithelial cells can help to identify the suspected tumor regions. Then other protein specific biomarkers are used to characterize the cancerous tissue. The regions stained by a specific biomarker can be identified and quantified and subsequently a score indicating the amount of positively stained tissue and negatively stained tissue can be visually estimated by pathologists. However, visual assessment by pathologists is prone to variability and subjectivity.

Thus, a computer-based method is sought for generating a repeatable and objective score of a histological diagnosis of a cancer patient, based on a precise estimation of tissue stained by a diagnostic antibody labeling cells that express a specific, cancer-treatment-related protein.

SUMMARY

The disclosed method uses a convolutional neural network model to determine how many pixels of an image patch that is cropped from a digital image of an immunohistochemically stained tissue belong to tissue that has been positively stained by a diagnostic antibody. The tissue that has been positively stained by the diagnostic antibody can be a specific cell, a specific group of cells or a specific type of cells present in the immunohistochemically stained tissue, for example, a macrophage or an epithelial cell or another cell that positively stains for the diagnostic antibody.

In a first step, a first image patch that is cropped from a digital image of a tissue slice immunohistochemically stained using a diagnostic antibody is loaded into a processing unit. In a second step, the first image patch is processed using a convolutional neural network to determine how many pixels of the first image patch belong to a first tissue that both belongs to tumor epithelium and that has been positively stained using the diagnostic antibody. The pixel-wise analysis of the image patch allows for high spatial resolution and precision in identifying tumor epithelium tissue that is positively stained using the diagnostic antibody. In a third step, additional image patches that have been cropped from the digital image are processed to determine how many pixels of each additional image patch belong to the first tissue. Then, the score of the histopathological diagnosis is computed based on the total number of pixels of the digital image that belong to the first tissue. The digital image and the score are displayed on a graphical user interface. In some embodiments, the score is the Tumor Cell (TC) score.

Another embodiment of the method includes performing image processing on an image patch using a generative adversarial network (GAN) to train a convolutional neural network to determine how many pixels of the image patch belong to (a) a first tissue that is both tumor epithelium and has been positively stained using a diagnostic antibody, (b) a second tissue that is both tumor epithelium and has been negatively stained using the diagnostic antibody, or (c) a third tissue that is neither the first tissue nor the second tissue. Consequently, both the first tissue and the second tissue are tumor epithelium. In one aspect, the second tissue is considered to be negatively stained if the tissue is not positively stained using the diagnostic antibody. Then, the score of the histopathological diagnosis is computed based on the total number of pixels that belong to the first tissue. The digital image and the score are displayed on a graphical user interface.

The convolutional neural network is trained using a generative adversarial network that transforms image patches generated on a stain domain A into fake patches of a stain domain B. A stain domain refers to the region of a digital image of tissue that has been stained for a specific biomarker. For example, the stain domain A is the tissue or the region of a digital image of a tissue that stains for a specific biomarker or stain such as cytokeratin (CK). The stain domain B, for example, is the tissue or the region of the digital image of the tissue that stains for a different specific biomarker or stain, such as programmed death ligand 1 (PD-L1). The generative adversarial network then transforms image patches generated by CK staining into fake patches that are realistic fakes of PD-L1 staining.

In another embodiment, a generative adversarial network is used to train a convolutional neural network to transform image patches generated on a stain domain A into fake patches of a stain domain B and then to perform segmentation on the stain domain B. For example, the generative adversarial network performs segmentation on the fake PD-L1 patches generated using CK staining to make realistic fakes of PD-L1 staining.

Another embodiment of the method involves training a convolutional neural network using two generative adversarial networks. A first of the two generative adversarial networks transforms image patches generated on a stain domain A into fake patches of a stain domain B. A second of the two generative adversarial networks transforms image patches generated on the stain domain B into fake patches of the stain domain A. For example, the first generative adversarial network transforms image patches generated by CK staining into fake patches that are realistic fakes of PD-L1 staining, and the second generative adversarial network transforms image patches generated using PD-L1 staining into fake patches that are realistic fakes of CK staining.

Another aspect of the disclosure concerns a system that generates a histopathological diagnosis for a cancer patient. The diagnostic system includes code that loads an image patch into a processing unit. The image patch is cropped from a digital image of a tissue slice. The image was acquired by scanning cancer tissue that was immunohistochemically stained using a diagnostic antibody. The system also includes code that processes the image patch using a convolutional neural network to determine whether each pixel of the image patch belongs to (a) a tumor epithelium tissue that has been positively stained using the diagnostic antibody, (b) a tumor epithelium tissue that was negatively stained using the diagnostic antibody, or (c) other tissue. The system also includes code for processing multiple image patches cropped from the image so as to compute a score for the histopathological diagnosis based on a total number of pixels determined to belong to the tumor epithelium tissue that was positively stained using the diagnostic antibody. The image and the score are then displayed on a graphical user interface of the system.

Other embodiments and advantages are described in the detailed description below. This summary does not purport to define the invention. The invention is defined by the claims.

BRIEF DESCRIPTION OF THE DRAWINGS

The accompanying drawings, where like numerals indicate like components, illustrate embodiments of the invention.

FIG. 9A is a real image of epithelial tissue with regions that have been positively stained with CK.

FIG. 9B is a synthetic image representing epithelial tissue positively stained with PD-L1 that was generated from the image of FIG. 9A by a convolutional neural network trained by a generative adversarial network.

FIG. 9C is a synthetic image representing epithelial tissue not positively stained with PD-L1 that was generated from the image of FIG. 9A.

FIG. 10A is a second real image of epithelial tissue with regions that have been positively stained with CK.

FIG. 10B is a second fake image representing epithelial tissue positively stained with PD-L1 that was generated from the real image of FIG. 10A.

FIG. 10C is another fake image representing epithelial tissue not positively stained with PD-L1 that was generated from the real image of FIG. 10A.

DETAILED DESCRIPTION

Reference will now be made in detail to some embodiments of the invention, examples of which are illustrated in the accompanying drawings.

Figure 1:
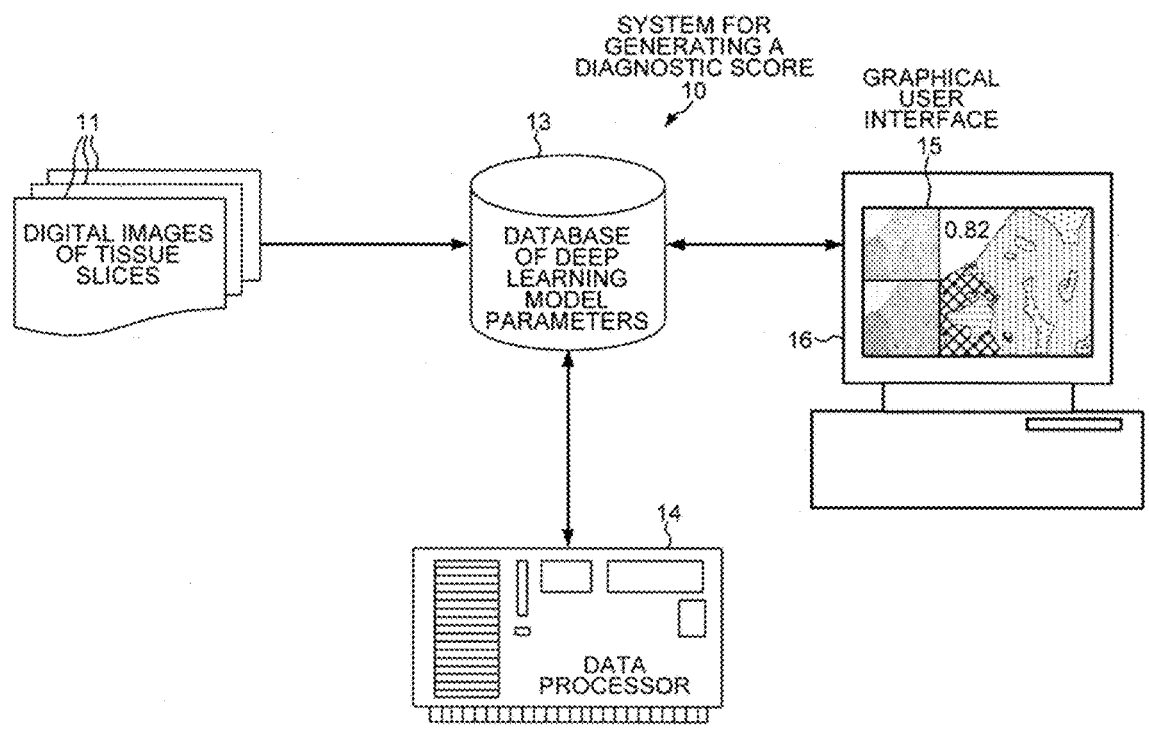
FIG. 1 is a diagram of a novel system for generating a histopathological diagnosis for a cancer patient by computing a sore for the histopathological diagnosis based on a total number of pixels determined to belong to tumor epithelium tissue that has been positively stained by a diagnostic antibody.

FIG. 1 shows a system 10 for generating a histopathological score for a cancer patient by computing a score for the histopathological diagnosis based on a total number of pixels determined to belong to tumor epithelial tissue that is positively stained by the diagnostic antibody. For example, the histopathological score is the Tumor Cell (TC) score. In one embodiment, the diagnostic antibody binds to the programmed death ligand 1 (PD-L1), and system 10 calculates a histopathological score for the cancer patient based on the total number of pixels of a digital image that have been determined to belong to tumor epithelium and to have been positively stained using the PD-L1 antibody. A high concentration of PD-L1 and thus a greater number of pixels determined to belong to tumor epithelium tissue that is positively stained by the PD-L1 antibody in solid tumors is indicative of a positive prognosis for patients treated by a PD-1/PD-L1 checkpoint inhibitor. Thus, system 10 analyzes digital images 11 to determine the total number of pixels that belong to first tissue that is positively stained using the diagnostic antibody PD-L1 and that is tumor epithelium. The first tissue is a specific group of tumor epithelial cells that are positively stained by the diagnostic antibody, in this embodiment by the PD-L1 antibody.

System 10 also identifies tissue that has been negatively stained by the diagnostic antibody. Tissue is considered to be "negatively stained" if the tissue is not positively stained by the diagnostic antibody. In this embodiment, the negatively stained tissue is tumor epithelial tissue that has not been positively stained by the PD-L1 antibody. The second tissue is a specific group of tumor epithelial cells that is negatively stained by the diagnostic antibody, in this embodiment by the PD-L1 antibody. In one embodiment, the first and second tissues that are positively and negatively stained by the diagnostic antibody belong to the same group of tumor epithelial cells. System 10 also identifies other tissue that belongs to different types of cells than the first and second tissues. The other tissue can be immune cells, necrotic cells, or any other cell type that is not the first or second tissue. The histopathological score computed by system 10 is displayed on a graphical user interface 15 of a user work station 16.

System 10 includes a convolutional neural network used for processing digital images and computing a score for the histopathological diagnosis of a cancer patient. The convolutional neural network is trained, wherein the training calculations are performed by a data processor 14. In one embodiment, data processor 14 is a specialized processor that can simultaneously perform multiple convolution operations between a plurality of pixel matrices and corresponding kernels. The logical operations of the model are implemented on data processor 14 as hardware, firmware, software, and/or a combination thereof to provide a means for characterizing regions of tissue in the digital image. Each trained model comprising an optimized set of parameters and associated mathematical operations is then stored in the database 13.

Once trained, system 10 reliably and precisely determines the total number of pixels that belong to tumor epithelium and that have been positively stained by the diagnostic antibody PD-L1. Training the convolutional neural network of system 10 by using a generative adversarial network obviates the need for extensive manual annotations of the digital images 11 that make up the training data set by transferring semi-automatically generated annotations on digital images of tissue stained with the epithelial cell marker CK to the PD-L1 domain. The biomarker CK specifically labels tumor epithelium, thereby allowing for a semi-automated segmentation of tumor epithelial regions based on the CK staining. After semantic segmentation, the digital images of tissue stained with the epithelial cell marker CK are transformed into the PD-L1 domain. During this step, synthetic or fake images are generated. The regions identified as epithelial cells (positive for CK staining) are labeled as being either positive for PD-L1 staining (PD-L1 expressing cells) or negative for PD-L1 staining (non-PD-L1 expressing cells). The resulting fake images of tissue stained with PD-L1 antibody that are generated based on the images of tissue stained using CK are then used in conjunction with a reduced number of images with manual annotations to train the convolutional neural network of system 10 to identify positively stained tissue in digital images of tissue stained with the PD-L1 antibody.

Figure 2:
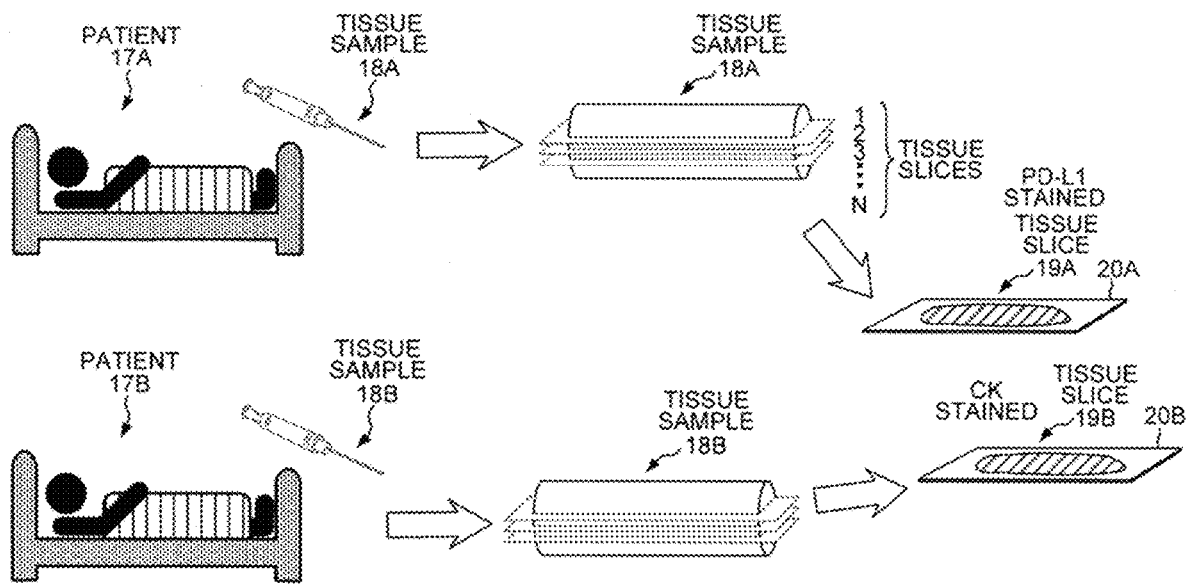
FIG. 2 illustrates the process of acquiring a digital image of a slice of tissue from a cancer patient that is stained with a diagnostic antibody, and the process of acquiring a digital image of a slice of tissue from another cancer patient that is stained with an antibody specific for epithelium.

FIG. 2 illustrates tissue samples 18A and 18B being taken from cancer patients 17A and 17B, respectively. A tissue slice 19A from tissue sample 18A is placed on a slide 20A and stained with a diagnostic antibody, such as the PD-L1 antibody. The tissue slice 19B is placed on the slide 20B and stained with a helper antibody, such as the CK antibody. The helper antibody is used only to train system 10, whereas the diagnostic antibody is used to compute the histopathological score in a clinical application of system 10. High resolution digital images are acquired from slice 19A and slice 19B of the tissue from cancer patients 17A and 17B. The tissue samples 18A and 18B can be taken from a patient suffering from non-small-cell lung cancer, other types of lung cancer, breast cancer, prostate cancer, pancreatic cancer or another type of cancer. In one embodiment, the tissue sample 18A is taken from a solid tumor. In another embodiment, the tissue sample has been stained with a PD-L1 antibody, and in yet another embodiment with an HER2 antibody. In some embodiments, regions that include normal epithelial cells (as opposed to tumor epithelium) are excluded from the digital images acquired from slice 19A and slice 19B.

Figure 3:
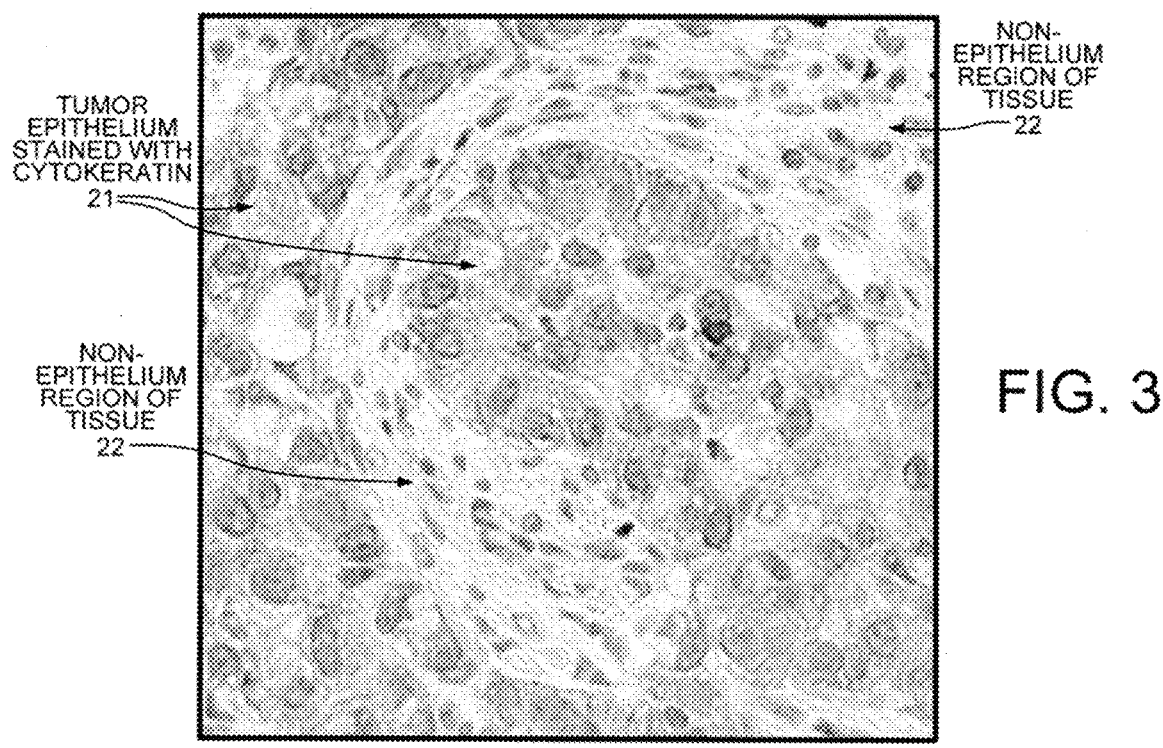
FIG. 3 is a digital image showing epithelial cells have been stained with cytokeratin (CK) and nuclei that have been stained with hematoxylin.

FIG. 3 shows a digital image acquired from slice 19B of the tissue from cancer patient 17B that has been stained using the CK antibody. Epithelial cells 21 are stained positive by the CK stain. Non-epithelial region 22 is not stained positively by the CK stain. The identification and segmentation of CK-positive epithelial cells and non-CK-positive other tissue is a first substep of the overall task of identifying epithelial cells that are positively stained using PD-L1.

Figure 4:
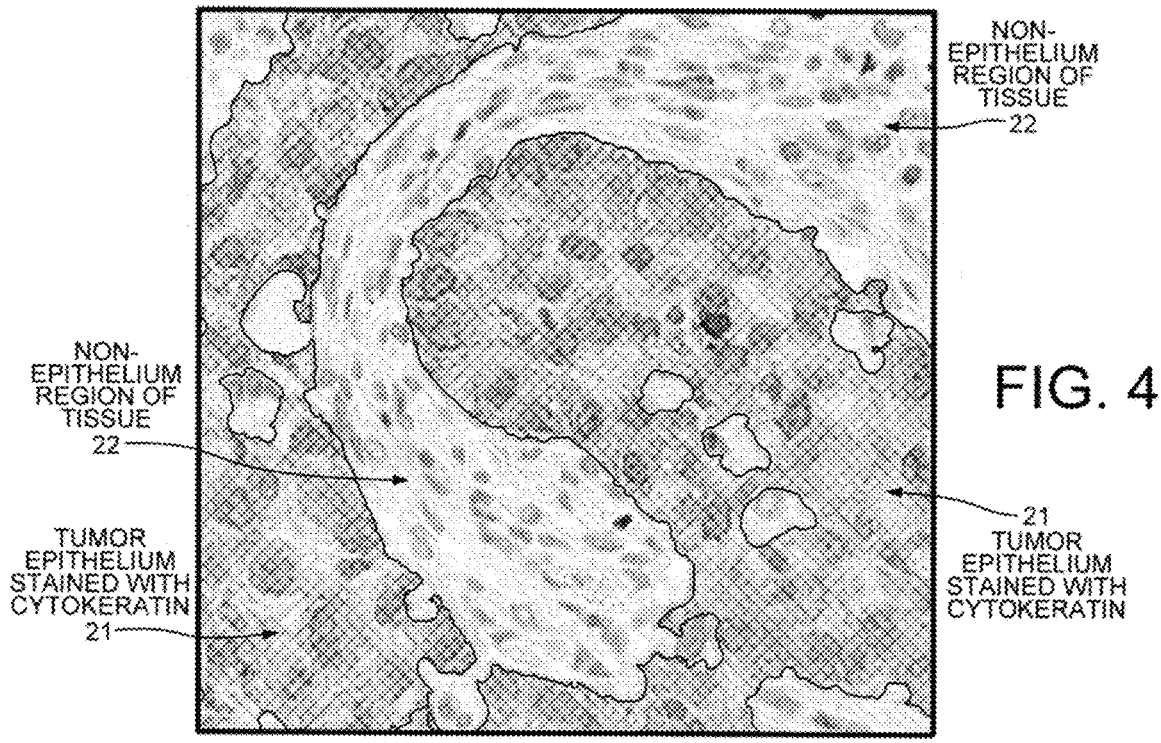
FIG. 4 shows the image of FIG. 3 in which the regions stained positively by CK are identified and segmented.

FIG. 4 shows the digital image of FIG. 3 in which the regions have been identified and segmented. The region 21 corresponding to CK-positively stained tissue has been marked with cross hatching and corresponds to tumor epithelium.

Figure 5:
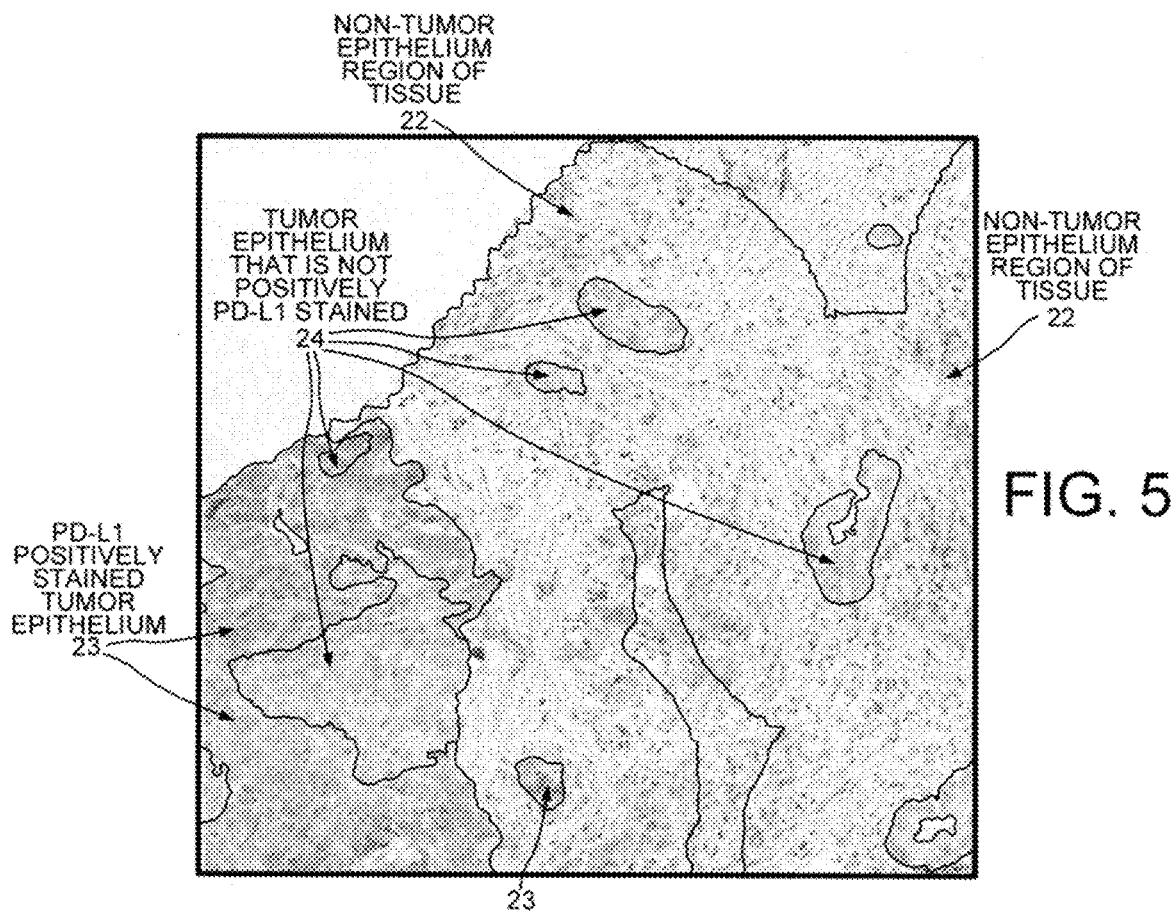
FIG. 5 is a digital image showing tissue that has been stained with a diagnostic antibody that stains PD-L1 and thus identifies regions in which the cells are positively stained epithelium, not-positively stained epithelium and non-epithelial.

FIG. 5 shows a digital image acquired from slice 19A of the tissue from cancer patient 17A that has been stained for the PD-L1 antibody. The digital image has been segmented into regions corresponding to regions 23 of tumor epithelial cells positively stained using the PD-L1 antibody, regions 24 of tumor epithelial cells that are not positively stained by the PD-L1 antibody, and regions 22 of other tissue (e.g., immune cells such as macrophages, necrotic tissue etc.). System 10 uses a convolutional neural network to determine for each pixel of the digital image whether that pixel belongs to tumor epithelial tissue positively stained by the PD-L1 antibody and thus belonging to region 23, tissue negatively (non-positively) stained by the PD-L1 antibody and thus belonging to region 24, or other tissue belonging to region 22. The score for the histopathological prognosis is calculated by dividing the total number of pixels determined to belong to the tumor epithelial tissue that is positively stained by the diagnostic antibody PD-L1 by the total number of pixels determined to belong both to the tumor epithelial tissue that is positively stained by the diagnostic antibody PD-L1 as well as to the tumor epithelial tissue that is not positively stained by the diagnostic antibody PD-L1 (regions 23 and 24).

Figure 6:
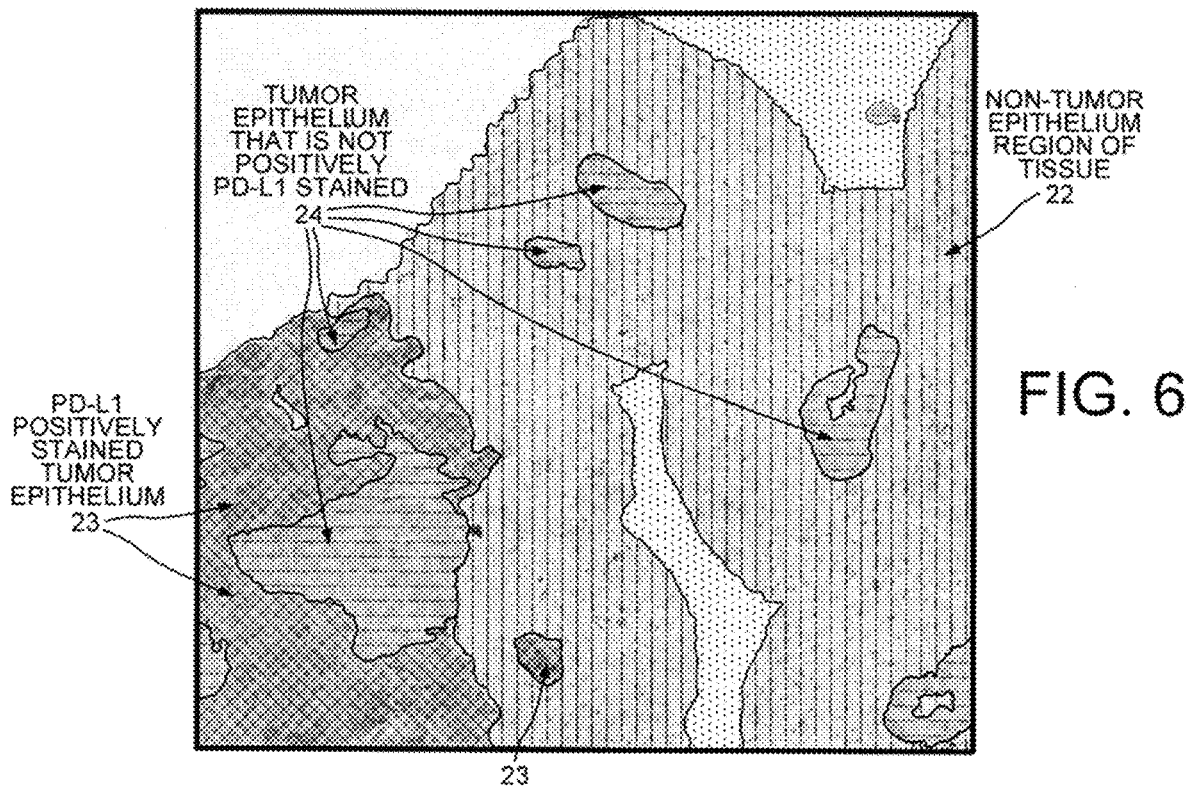
FIG. 6 shows the image of FIG. 5 with the region that is positively stained tumor epithelium marked with cross hatching, the region that is not not-positively stained tumor epithelium marked with horizontal lines and the region that is non-tumor epithelial tissue marked with vertical lines.

FIG. 6 shows the image of FIG. 5 segmented into the regions 22, 23 and 24. The region 23 corresponding to PD-L1-positively stained tumor epithelium is marked with cross hatching. The region 24 of tumor epithelium that is not PD-L1-positively stained is marked with horizontal lines. The region 22 that is non-epithelial tissue is marked with vertical lines.

Figure 7:
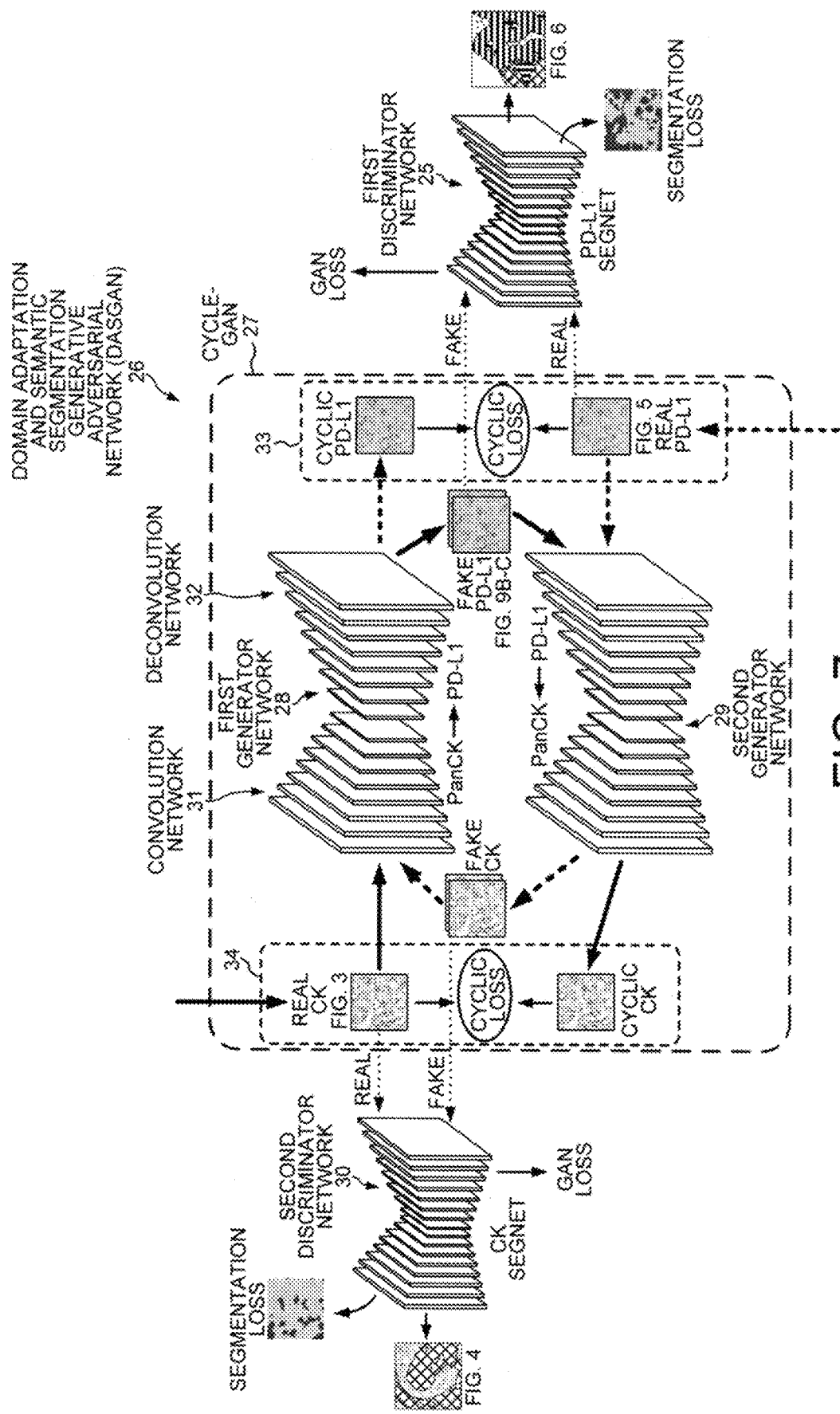
FIG. 7 illustrates (i) a convolutional neural network used to determine how many pixels of a first image patch belong to a first tissue that both belongs to tumor epithelium and that has been positively stained using a diagnostic antibody, and (ii) a generative adversarial network used to train the convolutional neural network.

FIG. 7 illustrates a convolutional neural network 25 used in a clinical application for determining how many pixels of a first image patch belong to a first tissue that has been positively stained by the diagnostic antibody PD-L1 and that belongs to tumor epithelium, and a generative adversarial network 26 used for training the convolutional neural network 25. The convolutional neural network 25 acts as a discriminator in the framework of the domain adaptation and semantic segmentation generative adversarial network (DASGAN) 26. In one embodiment, the DASGAN includes two generative adversarial networks that operate as a cycle forming a CycleGAN 27. The tissue slides stained with CK and PD-L1 that are used to train network 25 need not be from tissue of the same patient. Thus, FIG. 2 shows the PD-L1-stained tissue slice 19A coming from patient 17A and the CK-stained tissue slice 19B coming from patient 17B. When network 25 is deployed to generate a score, only the images of tissue slices stained by the diagnostic antibody, such as PD-L1, are used. Images of tissue slices stained by the helper antibody, such as CK, are used only for training the algorithm of the convolutional neural network 25. Network 25 is trained to recognize pixels of a first tissue that is associated with both fake CK positive staining and real PD-L1 positive staining.

The CycleGAN 27 includes two generative adversarial networks. The first of the two generative adversarial networks includes a first generator network 28 and a first discriminator network 25. The first generator network 28 transforms image patches generated on CK-stained tissue slices into fake patches of digital images of PD-L1 stained tissue slices. The first discriminator network 25 learns to distinguish digital images of real PD-L1 stained tissue slices from the fake images of PD-L1 stained tissue slices generated by the first generator network 28 and segments the PD-L1 positive and the PD-L1 negative regions in the digital images. The first generator network 28 transforms image patches generated on the stain domain of CK into fake patches of the stain domain of PD-L1. In some embodiments, the image patches in the stain domain of CK that are input into the first generator network 28 do not include any regions of normal epithelial cells but rather include only tumor epithelium. The fake patches in the stain domain of PD-L1 output by first generator network 28 thereby indicate only those PD-L1 stained regions that are also in tumor epithelium regions. In one embodiment, the first discriminator network 25 is used to determine how many pixels of an image patch belong to tumor epithelium tissue that has been positively stained by a diagnostic antibody, for example, by the PD-L1 antibody.

The second of the two generative adversarial networks includes a second generator network 29 and a second discriminator network 30. The second generator network 29 transforms image patches generated on PD-L1-stained tissue slices into fake patches of digital images of CK stained tissue slices. The second discriminator network 30 learns to distinguish digital images of real CK-stained tissue slices from the fake images of CK-stained tissue slices generated by the second generator network 29 and segments the CK positive and the CK negative regions in the digital images. The second generator network 29 transforms image patches generated on the stain domain of PD-L1 into fake patches of the stain domain of CK.

The first generator network 28, the second generator network 29, the first discriminator network 25 and the second discriminator network 30 each contain a convolution network and a deconvolution network that perform several layers of convolution and deconvolution steps, respectively. For example, the first generator network 28 includes a convolution network 31 and a deconvolution network 32.

The fake images of PD-L1 stained tissue slices generated by the first generator network 28 together with real images of PD-L1 stained tissue slices are fed into the second generator network 29 that generates fake images of CK stained tissue slices. The fake images of CK stained tissue slices generated by the second generator network 29 together with real images of CK stained tissue slices are fed into the first generator network 28 that generates fake images of PD-L1 stained tissue slices. For example, network 28 generates first fake images of tumor epithelium positively stained with the PD-L1 antibody as well as second fake images of PD-L1 negatively stained tumor epithelium.

To ensure the invertibility of the transformed domains (e.g., the domain of CK staining and the domain of PD-L1 staining), the CycleGAN 27 also includes cycle consistency losses 33-34. The network 28 transforms the fake CK images that have been generated by the network 29 from tissue slices that have been stained with PD-L1 back into the PD-L1 stain domain, thereby creating fake PD-L1 images from the fake CK images. The fake PD-L1 images generated by successively applying the generator network 29 and the generator network 28 are also referred to as "cyclic PD-L1" in FIG. 7. The network 29 transforms the fake PD-L1 images that have been generated by the network 28 from tissue slices that have been stained with CK back into the CK stain domain, thereby creating fake CK images from the fake PD-L1 images. The fake CK images generated by successively applying the generator network 28 and the generator network 29 are also referred to as "cyclic CK" in FIG. 7.

Figure 8:
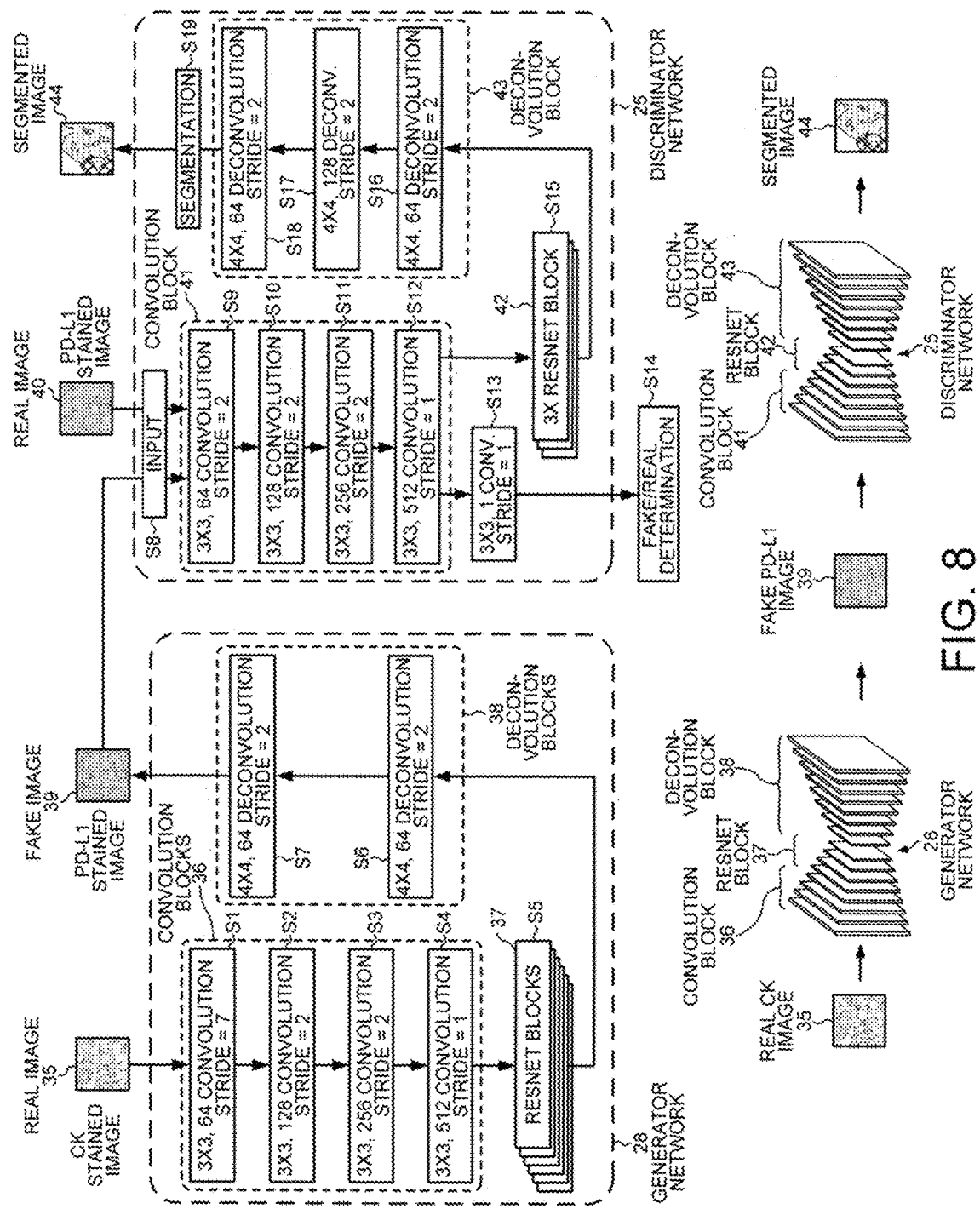
FIG. 8 shows in more detail the network architecture of the generative adversarial network (GAN) used to train the convolutional neural network.

FIG. 8 illustrates the first generator network 28 and the first discriminator network 25 of FIG. 7 in more detail. The first generator network 28 and the first discriminator network 25 form one of the generative adversarial networks of the CycleGAN 27. A real image 35, in this example a digital image of a CK-stained tissue slice, is input into the first generator network 28. The first generator network 28 includes a series of convolution blocks 36, of a series of residual network (ResNet) blocks 37 and of a series of deconvolution blocks 38. First generator network 28 performs several convolution, normalization and activation steps in convolution blocks 36. In a step S1, a convolution operation is carried out using a 3×3 operator with a stride of seven giving rise to a pixel patch with sixty-four convolution layers. In step S2, convolution is carried out using a 3×3 operator with a stride of two giving rise to pixels with 128 feature layers. In step S3, convolution is carried out on the 128 feature layers using a 3×3 operator with a stride of two giving rise to pixels with 256 feature layers. In step S4, convolution is carried out on the 256 feature layers using a 3×3 operator with a stride of one giving rise to pixels with 512 feature layers. Each convolution step is followed by an instance normalization step and a rectified linear unit (ReLu) activation step.

In step S5, six ResNet blocks 37 are applied before deconvolution commences in deconvolution block 38. The operations of the ResNet block 37 enable deep-layered networks to be trained with less computational burden on the network processing by allowing the information flow to bypass selected layers of the network. In step S6, deconvolution is carried out using a 4×4 operator with a stride of two giving rise to pixels with 64 feature layers. In step S7, deconvolution is carried out using a 4×4 operator with a stride of two giving rise to pixels with 64 feature layers. In step S7, deconvolution block 38 generates a fake image 39 in a different stain domain, in this example in the new domain of PD-L1 staining.

The first discriminator network 25 is then trained to segment PL-L1 images, whether fake or real, and to classify individual pixels as being stained by PL-L1 by using the fake PD-L1 images 39 generated by generator network 28 along with real PD-L1 images 40. In step S8, the fake image 39 output in step S7 is input into the first discriminator network 25 together with the real image 40 of the same stain domain, for example, a digital image that has been acquired from a tissue slice stained with PD-L1 antibody. For example, the first discriminator network 25 can be trained based on the fake PD-L1 images generated by the first generator network 28 and the associated ground-truth masks. The fake PD-L1 images generated by the first generator network 28 are then used for training in conjunction with manual annotations on real PD-L1 images acquired from tissue slices stained with PD-L1 antibody. In one embodiment, the complete DASGAN network 26, consisting of the network 27 (CycleGAN) and of the two SegNet networks 25 (PD-L1 SegNet) and 30 (CK SegNet) are trained simultaneously. Although "simultaneous" training still involves sequential steps on a computer, the individual optimizing steps of training both networks are interwoven.

The first discriminator network includes a convolution block 41, a ResNet block 42 and a deconvolution block 43. Several convolution, normalization and activation steps are performed in the convolution block 41. In step S9, convolution is carried out using a 3×3 operator with a stride of two giving rise to pixels with 64 feature layers. In step S10, convolution is carried out using a 3×3 operator with a stride of two giving rise to pixels with 128 feature layers. In step S11, convolution is carried out using a 3×3 operator with a stride of 2 giving rise to pixels with 256 feature layers. Each convolution step is followed by an instance normalization step and a rectified linear unit (ReLu) activation step. In step S13, convolution is carried out using a 3×3 operator with a stride of one giving rise to pixels with one feature layer. In step S14, the first discriminator network 25 determines the source of the input data, i.e., whether the image input into the discriminator 25 was a fake image of an PD-L1 staining generated by the generator 28 based on images of CK-stained tissue slices or a real image acquired from a tissue slice stained by PD-L1 antibody.

In step S15, three ResNet blocks 42 are applied to the convoluted image output by convolution block 41 in step S12. Then deconvolution block 43 performs deconvolution operations on the output of the ResNet blocks 42. In step S16, deconvolution is carried out using a 4×4 operator with a stride of 2 giving rise to pixels with 64 convolution layers. In step S17, deconvolution is carried out using a 4×4 operator with a stride of two giving rise to pixels with 128 layers. In step S18, deconvolution is carried out using a 4×4 operator with a stride of two giving rise to pixels with 64 layers. In step S19, the first discriminator network 25 performs segmentation to determine which pixels of the image patch belong to the first tissue that has been identified as positively stained for PD-L1. The classification as being positively stained for PD-L1 is performed on a pixel-by-pixel basis. The first discriminator network 25 also determines which pixels of the image patch belong to the second tissue that has been identified as not being positively stained (also known as being "negatively stained") for PD-L1. The first discriminator network 25 can also determine which pixels of the image patch belong to other tissue that corresponds to a different group of cells or cell type other than the first tissue or the second tissue. For example, the first tissue and second tissue can both be epithelial cells, and the other tissue can be immune cells.

FIG. 9A shows a real digital image 45 of a tissue slice stained with CK, with segmented regions of CK-positive epithelial cells. Because of the specificity of the CK biomarker to epithelium, epithelium regions are segmented on CK stained images using heuristic-based image analysis, for example color deconvolution followed by Otsu thresholding and morphological operations. Any remaining false positive detections are removed by manual annotation. In one example, the digital image 45 has 256×256 pixels. Epithelial cells are marked with the reference numeral 46, and non-epithelial tissue is marked with the reference numeral 48. Segmented images of tissue slices stained with CK are then input into the first generator network 28, which transforms the images of tissue slices stained for CK into synthetic or fake images corresponding to tissue stained with the PD-L1 antibody. The first generator network 28 thus performs image-to-image translation.

FIG. 9B shows a fake or synthetic image 49 of the PD-L1 antibody generated to be PD-L1 positive by the generator 28 from the real image 45 of FIG. 9A, with segmented regions 50 of PD-L1 positive cells generated from the segmented regions 46 of epithelium cells of FIG. 9A. Pixels in the regions of epithelium cells 46 in FIG. 9A are generated to be positively stained by PD-L1 in FIG. 9B, yielding the regions 50 to be classified as positively stained with PD-L1.

FIG. 9C shows a fake or synthetic image 51 of the PD-L1 antibody generated to be PD-L1 negative by the generator 28 from the real image 45 of FIG. 9A, with segmented regions 52 of PD-L1 negative cells generated from the segmented regions 46 of epithelium cells of FIG. 9A. Pixels in the regions of epithelium cells 46 in FIG. 9A are generated to be negatively stained by PD-L1 in FIG. 9C, yielding the regions 52 to be classified as negatively stained with PD-L1. Regions of fake image 51 are synthesized as PD-L1 negative using the knowledge of which cells were positively stained with CK in FIG. 9A combined with the trained deep learning knowledge of how the CK staining would correspond to negative PD-L1 staining. The fake images 49 and 51 have 128×128 pixels each. The first generator network 28 performs a "domain adaptation" from the CK stain domain to the PD-L1 stain domain by using segmented input images of CK-stained tissue.

FIG. 10A shows another example of a real digital image 53 of a tissue slice stained for CK, with segmented regions of CK-positive epithelial cells. Real image 53 has smaller regions of contiguous CK-stained epithelial cells than does real image 45 of FIG. 9A. Image 53 shows epithelial cells 54 stained positively for CK, and other tissue 48 that is not epithelial cells 54. These segmented images of tissue slices stained for CK are then input into the first generator network 28 that transforms the images of tissue slices stained for CK into fake images of tissue slices stained with the PD-L1 antibody.

FIG. 10B shows a fake or synthetic image 55 of the PD-L1 antibody generated to be PD-L1 positive by the generator 28 from the real image 53 of FIG. 10A, with segmented regions 56 of PD-L1 positive cells generated from the segmented regions 54 of epithelium cells of FIG. 10A. Pixels in the regions of epithelium cells 54 in FIG. 10A are generated to be positively stained by PD-L1 in FIG. 10B, yielding the regions 56 to be classified as positively stained with PD-L1. FIG. 10C shows a fake or synthetic image 57 of the PD-L1 antibody generated to be PD-L1 negative by the generator 28 from the real image 53 of FIG. 10A, with segmented regions 58 of PD-L1 negative cells generated from the segmented regions 54 of epithelium cells of FIG. 10A. Pixels in the regions of epithelium cells 54 in FIG. 10A are generated to be negatively stained by PD-L1 in FIG. 10C, yielding the regions 58 to be classified as negatively stained with PD-L1.

The stain used to make the real images operated upon by DASGAN 26 can be an antibody with a dye or a direct stain. The antibody can be a polyclonal antibody or a monoclonal antibody and can be directly conjugated with an entity allowing detection of the antibody or can be detected by use of a secondary antibody conjugated with an entity allowing detection of the antibody. The first tissue that has been positively stained by the diagnostic antibody includes tumor epithelial cell types. Examples of the diagnostic antibody include PD-L1, human epidermal growth factor receptor 2 (HER2), PD-L2, CTLA4 and CD73 antibodies. In other embodiments, the scoring is performed on cell types other than the CK positive epithelial cells. In those applications, the CK antibody is replaced by other cell-type-specific antibodies, such as CD20 for B-cells, CD34 for endothelial cells, CD3 for T-cells and CD68 for macrophages.

In order to train the first discriminator network 25, fake images of tissue slices stained with the PD-L1 antibody, which are generated by the first generator network 28, are input alongside real images of tissue slices stained with the PD-L1 antibody into the first discriminator network 25 at step S8 of FIG. 8. The first discriminator network 25 is trained to distinguish in step S14 the fake images of tissue slices stained with the PD-L1 antibody as generated by the first generator network 28 from the real images of tissue slices stained with the PD-L1 antibody. The first discriminator network 25 is also trained to perform segmentation on the PD-L1 images, both fake and real, to identify which pixels of the images belong to PD-L1 positive epithelial cells. Each pixel of the segmented image 44 of FIG. 8 is classified as belonging to a PD-L1 positively stained epithelial cell (the first tissue), an epithelial cell that is not positively stained by PD-L1, or other non-epithelial tissue. Segmentation maps are thus obtained as an output of the first discriminator network 25 in addition to the determination of whether an image is real or fake. The second discriminator network 30 performs the same operations on real and fake images in the CK stain domain.

In one embodiment, the first discriminator network 25 is deployed as a convolutional network to carry out the step of determining how many pixels of a first image patch belong to a first tissue that has been positively stained by the diagnostic antibody and that belongs to tumor epithelium. For example, the first tissue corresponds to tumor epithelial cells, and the diagnostic antibody is the PD-L1 antibody. In this case, the convolutional neural network determines which pixels of the first image patch belong to epithelial cells positively stained by the PD-L1 antibody.

Subsequently, a score of the histopathological diagnosis of the patient 17 is computed based on the total number of pixels of the image patch that have been determined to belong to a first tissue. For example, the score can be the Tumor Cell (TC) score. In one embodiment, the method involves selecting a therapy if the score obtained using the diagnostic antibody is larger than a predetermined threshold. The therapy that is selected uses a therapeutic antibody that binds to the protein targeted by the diagnostic antibody, e.g., to the PD-L1 protein targeted by the diagnostic antibody PD-L1.

For example, if a score of 0.6 is computed, this is indicative of 60% of the pixels in the image patch belonging to tumor epithelial tissue that has been positively stained by the PD-L1 antibody. The score is computed as the percentage of tumor epithelial cells that are PD-L1 positive. The score is calculated as the ratio of the total number of pixels that belong to the first tissue (e.g., tumor epithelial cells positively stained by the PD-L1 antibody) in relation to the total number of pixels that belong to the first tissue plus the second tissue (e.g., all tumor epithelial cells, including positively stained by the PD-L1 antibody as well as not positively stained by the PD-L1 antibody). In other words, a score of 0.6 indicates that 60% of the tumor epithelial cells in the tissue slice from which the digital image was acquired express the PD-L1 protein.

Evaluation of the score is performed using the predetermined threshold. For example, if the threshold of the score is set to 0.5, the computed score of 0.6 is above the threshold. In that case, a therapy is selected that uses a therapeutic antibody that binds to the protein (e.g., PD-L1) targeted by the diagnostic antibody (PD-L1). In this example, a PD1/PD-L1 check point inhibitor therapy would be selected.

In one example, the score is calculated as follows: the number of pixels in an image determined as belonging to the first tissue stained positively for the diagnostic antibody and belonging to tumor epithelium (e.g., PD-L1 positive epithelial cells) is 4,648,680. The number of pixels determined to correspond to the second tissue that belongs to tumor epithelium but that is not stained positively by the diagnostic antibody (e.g., PD-L1 negative epithelial cells) is 1,020,158. The Tumor Cell (TC) score is then calculated to be 0.820, which equals 4648680/(4648680+1020158).

Although the present invention has been described in connection with certain specific embodiments for instructional purposes, the present invention is not limited thereto. Various modifications, adaptations, and combinations of various features of the described embodiments can be practiced without departing from the scope of the invention as set forth in the claims.

What is claimed is:

1. A method of generating a score of a histopathological diagnosis of a cancer patient, comprising:
    loading a first image patch into a processing unit, wherein the first image patch is cropped from a digital image of a slice of tissue, and wherein the slice of tissue has been immunohistochemically stained using a diagnostic antibody;
    determining how many pixels of the first image patch belong to a first tissue that has been positively stained by the diagnostic antibody, wherein the determining is performed by processing each pixel of the first image patch using a convolutional neural network to recognize whether the processed pixel belongs to the first tissue based on other pixels in the first image patch;
    processing additional image patches that have been cropped from the digital image to determine how many pixels of each additional image patch belong to the first tissue;
    computing the score of the histopathological diagnosis based on a total number of pixels that belong to the first tissue; and
    displaying the digital image and the score on a graphical user interface.

2. The method of claim 1, wherein the determining how many pixels of the first image patch belong to the first tissue also involves determining how many pixels of the first image patch belong to a second tissue that has been negatively stained by the diagnostic antibody and to a third tissue that is neither the first tissue nor the second tissue.

3. The method of claim 1, wherein the convolutional neural network is trained using generative adversarial learning.

4. The method of claim 1, wherein the slice of tissue is taken from a biopsy of lung cancer.

5. The method of claim 1, wherein the diagnostic antibody is taken from the group consisting of: HER2, PD-L1, PD-L2, and CD73.

6. The method of claim 1, wherein the diagnostic antibody targets a protein, further comprising:
    selecting a therapy if the score obtained using the diagnostic antibody is larger than a predetermined threshold, wherein the therapy that is selected uses a therapeutic antibody that binds to the protein targeted by the diagnostic antibody.

7. The method of claim 6, wherein the diagnostic antibody is PD-L1, and wherein the selected therapy uses a PD-L1 medication if the score is larger than the predetermined threshold.

8. The method of claim 1, wherein the first tissue that has been positively stained by the diagnostic antibody includes cells taken from the group consisting of: epithelial cells, endothelial cells, stromal cells, macrophages, T cells and B cells.

9. A method of generating a score of a histopathological diagnosis of a cancer patient, comprising:
- loading a first image patch into a processing unit, wherein the first image patch is cropped from a digital image of a slice of tissue, and wherein the slice of tissue has been immunohistochemically stained using a diagnostic antibody;
- determining how many pixels of the first image patch belong to a first tissue that has been positively stained by the diagnostic antibody, wherein the determining is performed by processing the first image patch using a convolutional neural network, wherein the convolutional neural network is trained using generative adversarial learning, and wherein the convolutional neural network is trained using a generative adversarial network that transforms image patches generated on a stain domain A into fake patches of a stain domain B;
- processing additional image patches that have been cropped from the digital image to determine how many pixels of each additional image patch belong to the first tissue;
- computing the score of the histopathological diagnosis based on a total number of pixels that belong to the first tissue; and
- displaying the digital image and the score on a graphical user interface.

10. The method of claim 9, wherein the convolutional neural network is trained using two generative adversarial networks, wherein a first of the two generative adversarial networks transforms image patches generated on a stain domain A into fake patches of a stain domain B, and wherein a second of the two generative adversarial networks transforms image patches generated on the stain domain B into fake patches of the stain domain A.

11. A method of generating a score of a histopathological diagnosis of a cancer patient, comprising:
- loading a first image patch into a processing unit, wherein the first image patch is cropped from a digital image of a slice of tissue, and wherein the slice of tissue has been immunohistochemically stained using a diagnostic antibody;
- determining how many pixels of the first image patch belong to a first tissue that has been positively stained by the diagnostic antibody, wherein the determining is performed by processing the first image patch using a convolutional neural network, wherein the convolutional neural network is trained using generative adversarial learning, and wherein the convolutional neural network is trained using a generative adversarial network that is trained to transform image patches generated on a stain domain A into fake patches of a stain domain B and then to perform segmentation on the stain domain B;
- processing additional image patches that have been cropped from the digital image to determine how many pixels of each additional image patch belong to the first tissue;
- computing the score of the histopathological diagnosis based on a total number of pixels that belong to the first tissue; and
- displaying the digital image and the score on a graphical user interface.

12. The method of claim 11, wherein the convolutional neural network is trained using two generative adversarial networks, wherein a first of the two generative adversarial networks transforms image patches generated on a stain domain A into fake patches of a stain domain B and then performs segmentation on the stain domain B, and wherein a second of the two generative adversarial networks transforms image patches generated on the stain domain B into fake patches of the stain domain A and then performs segmentation on the stain domain A.

13. A method of generating a score of a histopathological diagnosis of a cancer patient, comprising:
- loading a first image patch into a processing unit, wherein the first image patch is cropped from a digital image of a slice of tissue, and wherein the slice of tissue has been immunohistochemically stained using a diagnostic antibody;
- determining how many pixels of the first image patch belong to a first tissue that has been positively stained by the diagnostic antibody, wherein the determining is performed by processing the first image patch using a convolutional neural network, and wherein the determining how many pixels of the first image patch belong to the first tissue also involves determining how many pixels of the first image patch belong to a second tissue that has been negatively stained by the diagnostic antibody and to a third tissue that is neither the first tissue nor the second tissue;
- processing additional image patches that have been cropped from the digital image to determine how many pixels of each additional image patch belong to the first tissue;
- computing the score of the histopathological diagnosis based on a total number of pixels that belong to the first tissue, wherein the score is a ratio of the total number of pixels that belong to the first tissue to a total number of pixels that belong to either the first tissue or the second tissue; and
- displaying the digital image and the score on a graphical user interface.

14. A method of generating a score of a histopathological diagnosis of a cancer patient, comprising:
- loading a first image patch into a processing unit, wherein the first image patch is cropped from a digital image of a slice of tissue, and wherein the slice of tissue has been immunohistochemically stained using a diagnostic antibody;
- determining how many pixels of the first image patch belong to a first tissue that has been positively stained by the diagnostic antibody, wherein the determining is performed by processing the first image patch using a convolutional neural network, and wherein the determining how many pixels of the first image patch belong to the first tissue also involves determining how many pixels of the first image patch belong to a second tissue that has been negatively stained by the diagnostic antibody and to a third tissue that is neither the first tissue nor the second tissue;
- processing additional image patches that have been cropped from the digital image to determine how many pixels of each additional image patch belong to the first tissue;
- computing the score of the histopathological diagnosis based on a total number of pixels that belong to the first tissue, wherein the score is a ratio of the total number of pixels that belong to the first tissue to a total number of pixels that belong to a selected tissue type, and wherein the selected tissue type is taken from the group consisting of: the first tissue, the second tissue and the third tissue; and displaying the digital image and the score on a graphical user interface.

15. A method of generating a score of a histopathological diagnosis of a cancer patient, comprising:
loading an image patch into a processing unit, wherein the image patch is cropped from a digital image of a slice of tissue, and wherein the slice of tissue has been immunohistochemically stained using a diagnostic antibody;
performing image processing on the image patch using a generative adversarial network to train a convolutional neural network to determine how many pixels of the image patch belong to (a) a first tissue that has been positively stained by the diagnostic antibody, (b) a second tissue that has been negatively stained by the diagnostic antibody, or (c) a third tissue that is neither the first tissue nor the second tissue, wherein the image processing is performed on each pixel of the image patch using the convolutional neural network to determine whether each pixel belongs to the first tissue;
computing the score of the histopathological diagnosis based on a total number of pixels that belong to the first tissue; and
displaying the score on a graphical user interface.

16. The method of claim 15, wherein the slice of tissue is lung tissue.

17. The method of claim 15, wherein the diagnostic antibody is taken from the group consisting of: HER2, PD-L1, PD-L2, and CD73.

18. The method of claim 15, wherein the score is a ratio of the total number of pixels that belong to the first tissue to a total number of pixels that belong to the second tissue.

19. The method of claim 15, further comprising:
recommending a therapy for the cancer patient that uses a therapeutic antibody that targets the same protein as that targeted by the diagnostic antibody if the score obtained using the diagnostic antibody is larger than a predetermined threshold.

20. The method of claim 19, wherein the diagnostic antibody is PD-L1, and wherein the therapy uses an anti-PD-L1 drug.

21. A method of generating a score of a histopathological diagnosis of a cancer patient, comprising:
loading an image patch into a processing unit, wherein the image patch is cropped from a digital image of a slice of tissue, and wherein the slice of tissue has been immunohistochemically stained using a diagnostic antibody;
performing image processing on the image patch using a generative adversarial network to train a convolutional neural network to determine how many pixels of the image patch belong to (a) a first tissue that has been positively stained by the diagnostic antibody, (b) a second tissue that has been negatively stained by the diagnostic antibody, or (c) a third tissue that is neither the first tissue nor the second tissue, wherein the convolutional neural network is trained using a cycle of two generative adversarial networks that jointly perform domain adaptation and segmentation;
computing the score of the histopathological diagnosis based on a total number of pixels that belong to the first tissue; and
displaying the score on a graphical user interface.

22. A system that generates a histopathological diagnosis for a cancer patient, comprising:
code for loading an image patch into a processing unit, wherein the image patch is cropped from an image of a tissue slice, and wherein the image was acquired by scanning cancer tissue that was immunohistochemically stained using a diagnostic antibody;
code for processing the image patch using a convolutional neural network to determine whether each pixel of the image patch belongs to (a) a tissue positively stained by the diagnostic antibody, (b) a tissue negatively stained by the diagnostic antibody, or (c) other tissue, wherein the convolutional neural network determines whether each pixel belongs to (a), (b) or (c) based on other pixels in the image patch;
code for processing multiple image patches cropped from the image so as to compute a score for the histopathological diagnosis based on a total number of pixels determined to belong to the tissue that is positively stained by the diagnostic antibody; and
a graphical user interface that displays the image and the score.

23. The system of claim 22, wherein if the score is larger than a predetermined threshold, then the system recommends a therapy that uses a therapeutic antibody that targets the same protein as that targeted by the diagnostic antibody.

24. The system of claim 23, wherein the diagnostic antibody is PD-L1, and wherein the therapy uses a drug targeting a protein of the group consisting of PD-L1 and PD-1.

25. A system that generates a histopathological diagnosis for a cancer patient, comprising:
code for loading an image patch into a processing unit, wherein the image patch is cropped from an image of a tissue slice, and wherein the image was acquired by scanning cancer tissue that was immunohistochemically stained using a diagnostic antibody;
code for processing the image patch using a convolutional neural network to determine whether each pixel of the image patch belongs to (a) a tissue positively stained by the diagnostic antibody, (b) a tissue negatively stained by the diagnostic antibody, or (c) other tissue, wherein the convolutional neural network is trained using a cycle of two generative adversarial networks that jointly perform domain adaptation and segmentation;
code for processing multiple image patches cropped from the image so as to compute a score for the histopathological diagnosis based on a total number of pixels determined to belong to the tissue that is positively stained by the diagnostic antibody; and
a graphical user interface that displays the image and the score.

* * * * *